(12) United States Patent
Okoniewski

(10) Patent No.: US 9,451,877 B2
(45) Date of Patent: *Sep. 27, 2016

(54) SINGLE PORT DEVICE HAVING INTEGRAL FILTER/VENT

(71) Applicant: Covidien LP, Mansfield, MA (US)

(72) Inventor: Gregory G. Okoniewski, North Haven, CT (US)

(73) Assignee: Covidien LP, Mansfield, MA (US)

( * ) Notice: Subject to any disclaimer, the term of this patent is extended or adjusted under 35 U.S.C. 154(b) by 93 days.

This patent is subject to a terminal disclaimer.

(21) Appl. No.: 14/054,908

(22) Filed: Oct. 16, 2013

(65) Prior Publication Data

US 2014/0051933 A1 Feb. 20, 2014

Related U.S. Application Data

(63) Continuation of application No. 12/845,135, filed on Jul. 28, 2010, now Pat. No. 8,585,632.

(60) Provisional application No. 61/230,200, filed on Jul. 31, 2009.

(51) Int. Cl.
| | | |
|---|---|---|
| *A61M 37/00* | (2006.01) | |
| *A61M 31/00* | (2006.01) | |
| *A61M 5/178* | (2006.01) | |
| *A61B 1/32* | (2006.01) | |
| *A61B 17/34* | (2006.01) | |
| *A61M 13/00* | (2006.01) | |
| *A61B 17/00* | (2006.01) | |

(52) U.S. Cl.
CPC .............. *A61B 1/32* (2013.01); *A61B 17/3423* (2013.01); *A61M 13/003* (2013.01); *A61B 17/3474* (2013.01); *A61B 2017/00022* (2013.01); *A61B 2017/00115* (2013.01); *A61B 2017/00199* (2013.01); *A61B 2017/3429* (2013.01); *A61B 2218/006* (2013.01)

(58) Field of Classification Search
CPC A61B 17/3423; A61B 17/3474; A61B 1/32; A61B 2017/00022; A61B 2017/3429; A61B 2218/006; A61M 13/003; A61M 5/165; A61M 2005/1652; A61M 2005/1655; A61M 2005/1657

See application file for complete search history.

(56) References Cited

U.S. PATENT DOCUMENTS

| 4,737,148 A | 4/1988 | Blake |
| 5,318,516 A | 6/1994 | Cosmescu |

(Continued)

FOREIGN PATENT DOCUMENTS

| EP | 0950376 | 10/1999 |
| EP | 1188415 | 3/2002 |

(Continued)

OTHER PUBLICATIONS

U.S. Appl. No. 13/091,246, filed Apr. 21, 2011, Paul D. Richard.

(Continued)

*Primary Examiner* — Rebecca E Eisenberg

(57) ABSTRACT

A laparoscopic port device includes a compliant port body having a distal and proximal end having a lumen extending therethrough. The lumen has a filtering agent configured to retain or treat particulate contaminates present in insufflation gases. The laparoscopic port device further includes a valve operatively connected with the lumen to selectively regulate flow of the insufflation gases therethrough.

8 Claims, 7 Drawing Sheets

(56) References Cited

U.S. PATENT DOCUMENTS

| | | | |
|---|---|---|---|
| 5,336,169 | A | 8/1994 | Divilio et al. |
| 5,451,222 | A | 9/1995 | De Maagd et al. |
| 5,709,675 | A | 1/1998 | Williams |
| 5,722,962 | A | 3/1998 | Garcia |
| 5,914,415 | A | 6/1999 | Tago |
| 6,042,573 | A | 3/2000 | Lucey |
| 6,544,210 | B1 | 4/2003 | Trudel |
| 6,589,316 | B1 | 7/2003 | Schultz et al. |
| 6,592,543 | B1 | 7/2003 | Wortrich |
| 6,685,665 | B2 | 2/2004 | Booth et al. |
| 6,725,080 | B2 | 4/2004 | Melkent et al. |
| 6,890,295 | B2 | 5/2005 | Michels et al. |
| 6,991,602 | B2 | 1/2006 | Nakazawa et al. |
| 7,258,712 | B2 | 8/2007 | Schultz |
| 7,798,898 | B2 | 9/2010 | Luciano, Jr. et al. |
| 2002/0128603 | A1* | 9/2002 | Booth ............... A61B 17/3421 604/164.01 |
| 2006/0069306 | A1 | 3/2006 | Banik et al. |
| 2006/0247499 | A1 | 11/2006 | Butler et al. |
| 2009/0093752 | A1 | 4/2009 | Richard et al. |
| 2009/0137943 | A1 | 5/2009 | Stearns et al. |
| 2009/0326332 | A1 | 12/2009 | Carter |
| 2010/0241061 | A1 | 9/2010 | Ott et al. |
| 2011/0166506 | A1* | 7/2011 | Ott et al. .................. 604/26 |
| 2011/0251463 | A1 | 10/2011 | Kleyman |
| 2011/0251464 | A1 | 10/2011 | Kleyman |
| 2011/0251465 | A1 | 10/2011 | Kleyman |
| 2011/0251466 | A1 | 10/2011 | Kleyman et al. |

FOREIGN PATENT DOCUMENTS

| | | |
|---|---|---|
| EP | 1774918 | 4/2007 |
| EP | 2044889 | 4/2009 |
| WO | 97/11642 A1 | 4/1997 |
| WO | WO 97/33520 | 9/1997 |
| WO | WO 99/16368 | 4/1999 |
| WO | WO 2008/015566 | 2/2008 |
| WO | WO 2008/042005 | 4/2008 |
| WO | WO 2008/077080 | 6/2008 |

OTHER PUBLICATIONS

U.S. Appl. No. 13/031,352, filed Feb. 21, 2011, Gennady Kleyman.
U.S. Appl. No. 13/193,647, filed Jul. 29, 2011, Russell Pribanic.
U.S. Appl. No. 13/217,717, filed Aug. 25, 2011, Joshua Stopek.
U.S. Appl. No. 13/221,062, filed Aug. 30, 2011, Gregory Okoniewski.
U.S. Appl. No. 13/223,029, filed Sep. 1, 2011, Michael Davis.
U.S. Appl. No. 13/223,330, filed Sep. 1, 2011, Gregory Okoniewski.
U.S. Appl. No. 13/223,336, filed Sep. 1, 2011, Michael Davis.
U.S. Appl. No. 13/223,613, filed Sep. 1, 2011, Greg Fischvogt.
U.S. Appl. No. 13/223,627, filed Sep. 1, 2011, Gregory Okoniewski.
U.S. Appl. No. 13/223,645, filed Sep. 1, 2011, Gennady Kleyman.
U.S. Appl. No. 13/223,659, filed Sep. 2, 2011, Francesco Alfieri.
U.S. Appl. No. 13/223,678, filed Sep. 1, 2011, Gregory Okoniewski.
U.S. Appl. No. 13/223,700, filed Sep. 1, 2011, Gennady Kleyman.
U.S. Appl. No. 13/224,353, filed Sep. 2, 2011, Gennady Kleyman.
U.S. Appl. No. 13/224,354, filed Sep. 2, 2011, Greg Okoniewski.
U.S. Appl. No. 13/224,355, filed Sep. 2, 2011, Anibal Rodrigues Jr.
U.S. Appl. No. 13/224,358, filed Sep. 2, 2011, Andrew Barnes.
U.S. Appl. No. 13/228,937, filed Sep. 9, 2011, Dino Kasvikis.
U.S. Appl. No. 13/228,960, filed Sep. 9, 2011, Russell Pribanic.
European Search Report EP08253236 dated Feb. 10, 2009.
European Search Report EP09251613 dated Mar. 24, 2011.
European Search Report EP10250526 dated Jun. 23, 2010.
European Search Report EP10250638 dated Jul. 19, 2010.
European Search Report EP10250643 dated Jun. 23, 2010.
European Search Report EP10250881 dated Aug. 18, 2010.
European Search Report EP10250885 dated Aug. 18, 2010.
European Search Report EP10250944 dated Jul. 29, 2010.
European Search Report EP10251218 dated Jun. 15, 2011.
European Search Report EP10251317 dated Oct. 15, 2011.
European Search Report EP10251399 dated Sep. 13, 2010.
European Search Report EP10251486 dated Oct. 19, 2010.
European Search Report EP10251693 dated Feb. 3, 2011.
European Search Report EP10251718 dated Jan. 28, 2011.
European Search Report EP10251751 dated Apr. 28, 2011.
European Search Report EP10251796 dated Jan. 31, 2011.
European Search Report EP10251955 dated Feb. 21, 2011.
European Search Report EP10251983 dated Feb. 15, 2011.
European Search Report EP10251984 dated Feb. 10, 2011.
European Search Report EP10251985 dated Feb. 15, 2011.
European Search Report EP10251986 dated Mar. 7, 2011.
European Search Report EP 10 25 1359 completed Nov. 8, 2010.
Canadian Office Action issued in corresponding Canadian Appln. No. 2,711,350 dated May 13, 2016.

* cited by examiner

SINGLE PORT DEVICE HAVING INTEGRAL FILTER/VENT

CROSS REFERENCE TO RELATED APPLICATION

The present application is a continuation of U.S. patent application Ser. No. 12/845,135 filed Jul. 28, 2010, now U.S. Pat. No. 8,585,632, which claims priority to, and the benefit of, U.S. Provisional Patent Application Ser. No. 61/230,200, filed on Jul. 31, 2009, the entire contents of each of these prior applications are incorporated herein by reference.

TECHNICAL FIELD

The present disclosure relates to seals for use in a surgical procedure. Specifically, the present disclosure relates to seal anchor members adapted for insertion into an incision in tissue, and, more particularly to devices for removal of contaminants from insufflation gases utilizing said insert.

BACKGROUND

Today, many surgical procedures are performed through small incisions in the skin, as compared to the larger incisions typically required in traditional procedures, in an effort to reduce both trauma to the patient and recovery time. Generally, such procedures are referred to as "endoscopic", unless performed on the patient's abdomen, in which case the procedure is referred to as "laparoscopic". Throughout the present disclosure, the term "minimally invasive" should be understood to encompass both endoscopic and laparoscopic procedures.

During a typical minimally invasive procedure, surgical objects, such as surgical access devices, e.g., trocar and cannula assemblies, or endoscopes, are inserted into the patient's body through the incision in tissue. In general, prior to the introduction of the surgical object into the patient's body, insufflation gasses are used to enlarge the area surrounding the target surgical site to create a larger, more accessible work area. Accordingly, the maintenance of a substantially fluid-tight seal is desirable so as to inhibit the escape of the insufflation gases and the deflation or collapse of the enlarged surgical site.

To this end, various valves and seals are used during the course of minimally invasive procedures and are widely known in the art. However, a continuing need exists for a seal anchor member that can be inserted directly into the incision in tissue and that can accommodate a variety of surgical objects while maintaining the integrity of an insufflated workspace.

Further, the insufflation gases may become contaminated in the course of a surgery by the incidental byproducts of a procedure such as smoke or moisture. If the contaminated insufflation gases are released from the patient's body into the extra-corporeal environment, i.e. the operating room, the contaminated insufflation gases may then interfere with the surgeon's line of sight as well as contaminate the operating environment, in turn, adversely affecting the normal operation of the surgical procedure. Solutions to this problem known in the art involve the use of valves, stopcocks, and additional tubing to purify or replace the contaminated insufflation gases.

SUMMARY

A surgical apparatus is herein disclosed which traverses a bodily membrane and allows for the filtration of insufflation gases. A laparoscopic port device includes a port body having a distal and proximal end with a lumen extending therethrough. The at least one lumen may be substantially occupied by a filtering agent configured to retain particulate contaminates present in insufflation gases and, optionally, a second lumen extending through the port body configured to allow surgical instruments to traverse the port body.

In one embodiment, the surgical apparatus further includes a valve fluidly coupled to the at least one lumen occupied by the filtering agent. The valve defines a dynamically adjustable opening therein to regulate the flow rate of fluids or gases through the at least one lumen. The valve may be a component integrated with the port body or separated from the port body. The valve may be disposed within the port body or disposed external to the port body.

In a certain embodiment, the valve is manually operated. In another embodiment, the valve is electrically operated, driven by a control unit through a control signal. The control unit instructs the valve to dynamically adjust its opening to regulate the flow rate through the lumen occupied by the filtering agent.

In a further embodiment, the surgical apparatus includes a work station that comprises the control unit discussed above, as well as a display unit. The surgical apparatus further includes an insufflation instrument and an endoscope inserted through the laparoscopic port device, as well as the valve discussed above. The work station is configured to instruct the insufflation instrument to regulate the input rate of the insufflation sources. The work station is also configured to instruct the valve to regulate the flow rate of fluids or gases therethrough. The work station is further configured to receive, display and analyze images transmitted by the endoscope, thereby sending instructions to the insufflation device and valve accordingly based on the analysis.

It is further contemplated that the surgical apparatus may be a laparoscopic port device including; a port body which is substantially composed of a filtering agent configured to retain particulate contaminates present in insufflation gases and optionally a lumen extending through the port body configured to allow surgical instruments to traverse the port body.

BRIEF DESCRIPTION OF THE DRAWINGS

Various embodiments of the present disclosure are described hereinbelow with references to the drawings, wherein.

DETAILED DESCRIPTION OF THE EMBODIMENTS

Figure 1:
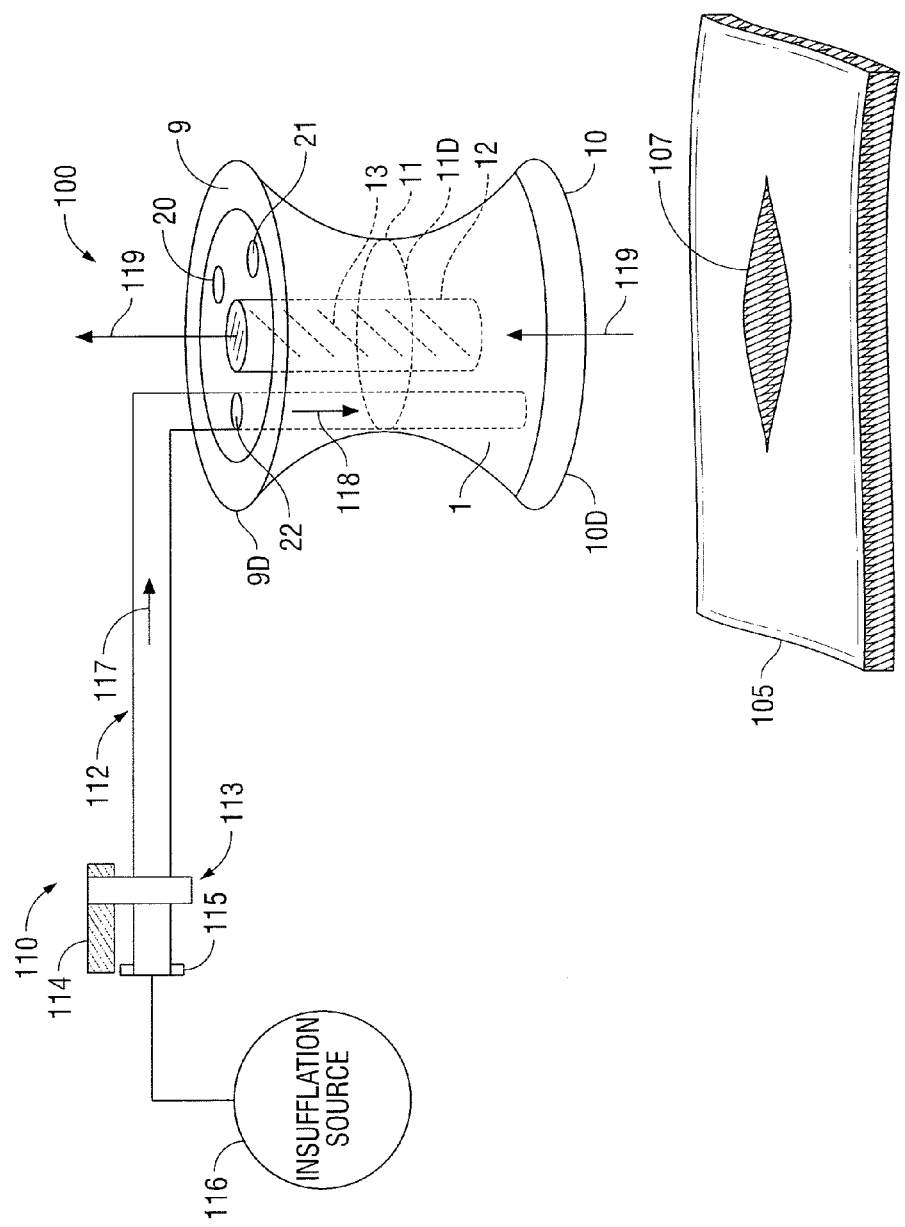
FIG. 1 shows a perspective view of a single port device having an integral filter/vent.

While embodiments of the present disclosure are susceptible to various modifications and alternative constructions, certain illustrated embodiments thereof have been shown in the drawings and will be described below in detail. It should be understood, however, that there is no intention to limit the embodiments of the present disclosure to the specific form disclosed, but, on the contrary, the embodiments are intended to cover all modifications, alternative constructions, and equivalents falling within the spirit and scope of the present disclosure as defined in the claims.

In the drawings and in the description which follows, in which like references numerals identify similar or identical elements, the term "proximal" will refer to the end of the apparatus which is closest to the clinician during use, while the term "distal" will refer to the end which is furthest from the clinician, as is traditional and known in the art.

One type of minimal invasive surgery described herein is multiple instrument access through a single surgical port. This technique is a minimally invasive surgical procedure, which permits a surgeon to operate through a single entry point, typically the patient's navel. The disclosed procedure involves insufflating the body cavity and with a housing member positioned within an opening in the patient's skin. Instruments including an endoscope and additional instruments such as graspers, staplers, forceps or the like may be introduced within the port to carry out the surgical procedure. The presently disclosed access port may be used with a surgically created incision, a naturally occurring opening such as the anus or the vagina, or in non-laparoscopic procedures.

FIG. 1 shows an embodiment of the presently disclosed access port relative to a skin incision. The seal anchor member 100 includes a body 1 which is a temporary percutaneous implant configured to traverse the skin 105 of a patient through an incision 107 thereof. Although the embodiment in FIG. 1 shows a percutaneous implant, it is contemplated that body 1 could traverse any biological barrier to provide selective communication between the volumes on opposing sides of the barrier. These include inter and intra organ barriers as well systemic barriers within the body.

The body 1 of the access port has a generally cylindrical form with a proximal surface 9 having a first diameter 9D and a distal surface 10 having a second diameter 10D with a medial plane 11 having a diameter 11D disposed therebetween such that 11D is less than 10D and 9D defining a profile which narrows near the medial plane and widens at the proximal surface 9 and distal surface 10 defining a generally hourglass configuration.

Although FIG. 1 shows proximal surface 9 and distal surface 10 as planar, it is contemplated that the profile of either surface could be arcuate such that the surface is concave to facilitate the placement of surgical implements or convex to facilitate the removal of fluid from the surface.

The body 1 comprises a plurality of lumens 20, 21 and 22 configured to allow the insertion and manipulation of surgical apparatus through body 1. One of the plurality of lumens, such as lumen 22 as illustrated in FIG. 1, serves as an insufflation fluid delivery channel. The lumen 22 connects with an insufflation instrument 110. The insufflation instrument 110 may be any suitable instrument adapted to convey fluids or introduce insufflation fluids, e.g., $CO_2$ into the peritoneal cavity or other subcutaneous spaces. The insufflation instrument 110 includes housing 113 and elongated member 112 extending from the housing 113. Housing 113 incorporates a stop cock valve 114 to permit selective passage and interruption of fluids. Housing 131 further includes a luer connector 115 adjacent to stop cock valve 114. The luer connector 115 is adapted for connection to an insufflation source 116 such as $CO_2$ utilized to insufflate the peritoneal cavity. Elongated member 112 defines a fluid conduit in communication with stop cock valve 114 to deliver passage of fluids into the peritoneal cavity in the direction indicated by the arrow signs 117 and 118.

It is further contemplated that body 1 is composed of a substantially compliant or compressible material such that when body 1 is inserted into an incision, the tissue disposed along the sides of the incision compresses body 1 with the resultant restorative force between body 1 and the tissue defining a sealing pressure therebetween. The sealing pressure forms a substantially fluid tight seal with its surrounding tissue which separates the volumes which body 1 traverses, e.g. between an insufflated cavity and the extra-corporeal environment.

With further reference to FIG. 1, integral vent 12 traverses body 1 defining lumen 13 which is configured to allow limited gaseous or fluid communication between the otherwise separated volumes at the distal and proximal ends of body 1. For instance, gases or fluids may exit from the high pressure peritoneal cavity through integral vent 12 to the low pressure extra-corporeal environment in the direction indicated by the directional arrow 119 for purposes of achieving an equilibrium pressure between the peritoneal cavity and the extra-corporeal environment. A filtering agent such as a particulate filter, activated charcoal, or open cell foam is disposed in lumen 13 of integral vent 12. The filtering agent is capable of capturing a significant amount of contaminants present in gases passing through lumen 13.

It is further contemplated that the filtering agent contains a portion of a compound such as a catalyst or activated charcoal whereby the compound treats or reacts with the contaminated insufflation gases or fluid.

The use and function of seal anchor member 100 will be discussed during the course of a typical minimally invasive procedure. Initially, the seal anchor member 100 is first inserted into a tissue tract 107 using known surgical techniques. Next, the insufflation instrument 110 is coupled to the seal anchor member 100 for introducing insufflation gases into a peritoneal cavity. The input rate of the insufflation gases into the peritoneal cavity is initially greater than the output rate of gases or fluids through the lumen 13 of the integral vent 12, such that the peritoneal cavity is insufflated. Once the peritoneal cavity reaches it desired insufflation volume and/or its desired insufflation pressure, the input rate of the insufflation sources is reduced to be substantially the same as the output rate of gases or fluids through the lumen 13, resulting in an equilibrium state. In the equilibrium state, the same desired insufflation volume and/or the same desired insufflation pressure are constantly maintained within the peritoneal cavity providing a proper working environment for conducting the minimally invasive procedure. In the course of a minimally invasive procedure, when a portion of the insufflation gases within the cavity is contaminated by smoke or other similar byproducts, the output rate of the gases may be selectively increased to facilitate removal of the contaminants from the cavity through the filter. As needed, input rate of the insufflation gases from the insufflation instrument may also be selectively increased to introduce more insufflation gases to compensate for the escape of contaminated gases.

Figure 2:
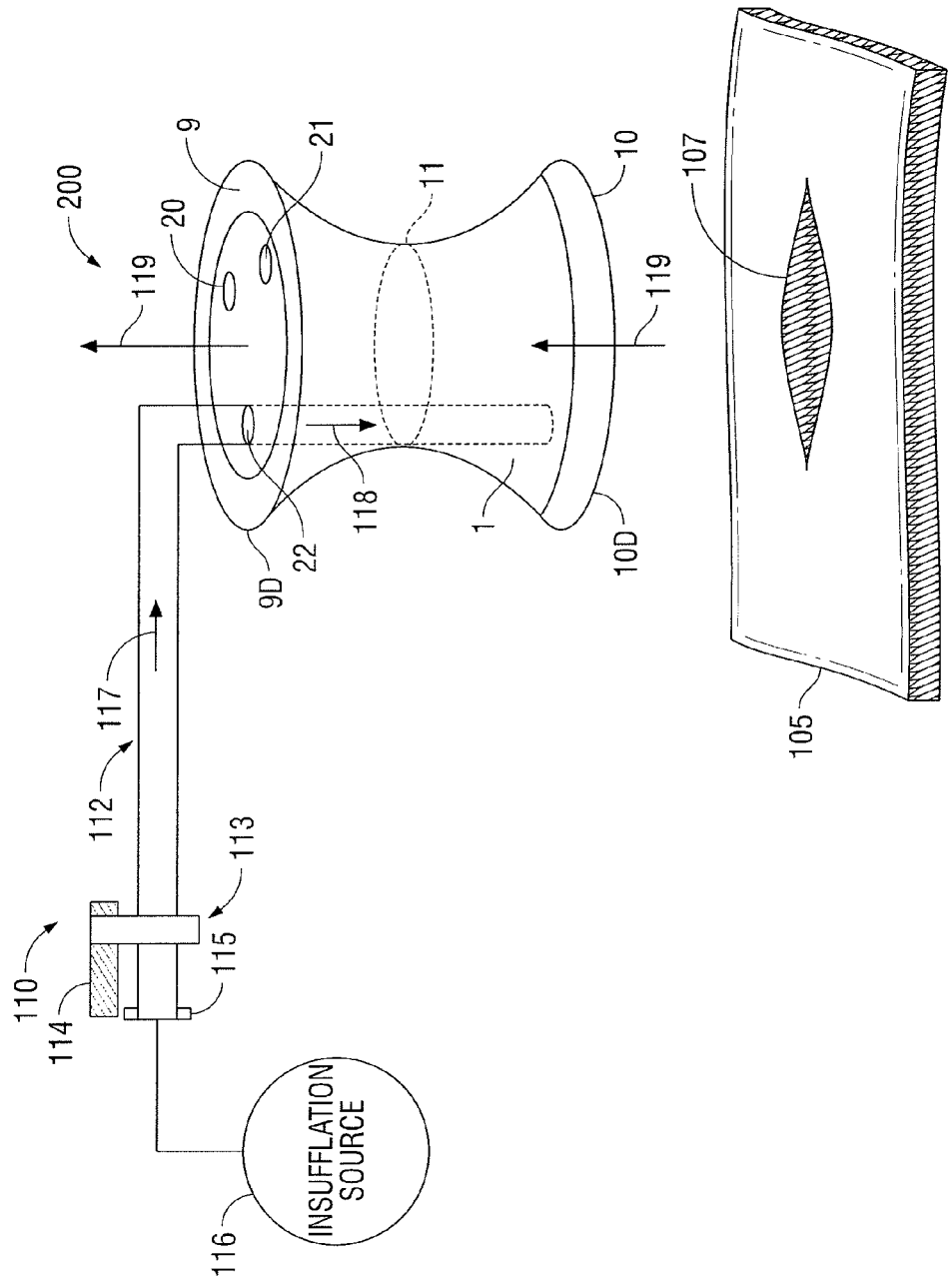
FIG. 2 shows a perspective view of a single port device having a substantially porous construction.

With reference to FIG. 2, seal anchor member 200 is shown wherein body 1 is substantially composed of a porous filtering agent such as a particulate filter, activated charcoal, open cell foam, or other material known to have advantageous filtering properties. In such a configuration, body 1 allows limited gaseous or fluid communication between the otherwise separated volumes at the distal and proximal ends of body 1. For instance, gases or fluids may exit from the high pressure peritoneal cavity through the material of body 1 to the low pressure extra-corporeal environment in the direction indicated by the directional arrow 119 to achieve equilibrium. The operation of the seal anchor member 200 is similar to that of the seal anchor member 100 described above. Specifically, the input rate of the insufflation sources can be regulated to first exceed the output rate of gases or fluids through body 1 until the peritoneal cavity reaches the desired insufflation volume and the desired insufflation pressure. The input rate of the insufflation sources is then reduced to be the same as the output rate through body 1 for purposes of maintaining the desired insufflation volume and the desired insufflation pressure.

Further, similar to seal anchor member 100 illustrated in FIG. 1, seal anchor member 200 comprises a plurality of lumens 20, 21 and 22, and one of which is in connection with the insufflation instrument 110 for introducing insufflation gases into the body cavity.

Figure 3:
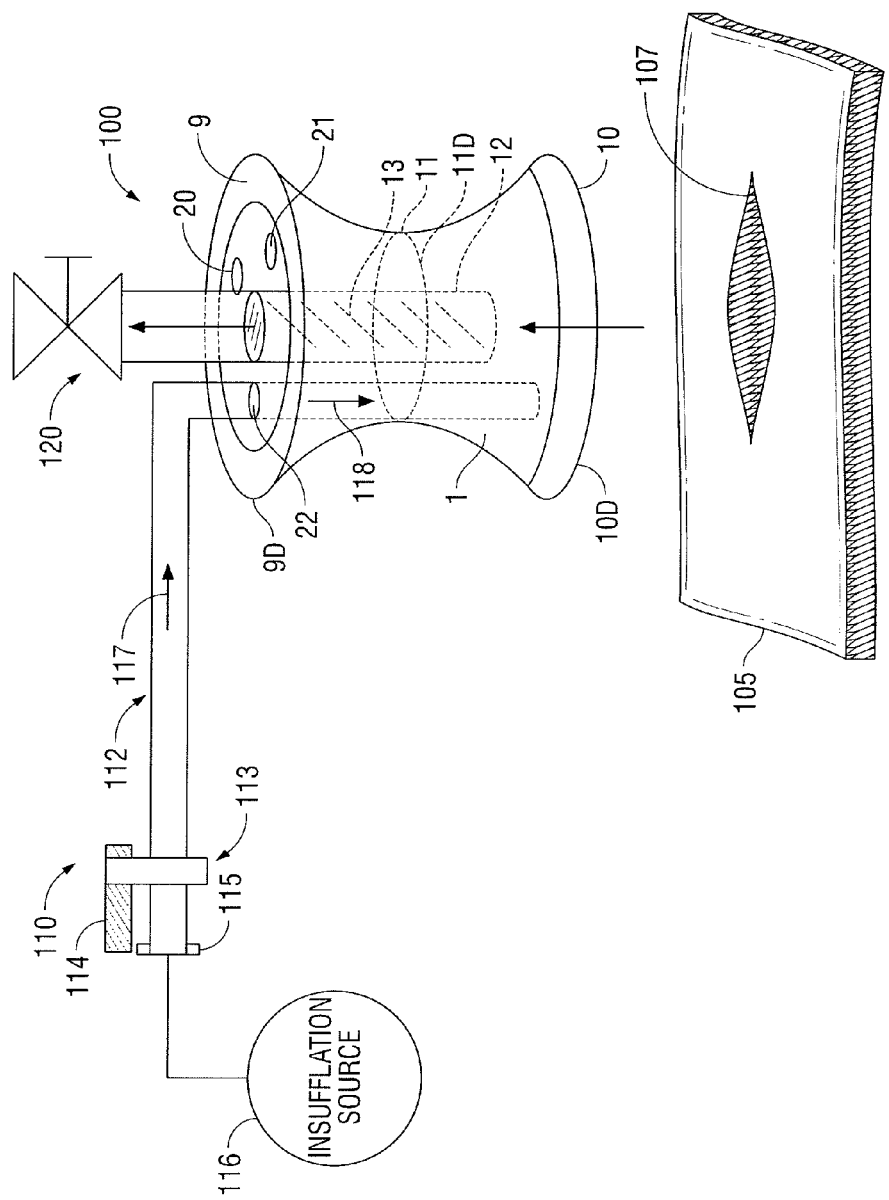
FIG. 3 shows a perspective view of the single port device of FIG. 1 in connection with a manually-controlled external valve.

With reference to FIG. 3, the seal anchor member 100 may further include a valve 120 operatively connected with the lumen 13 of the integral vent 12. The valve 120 is configured to selectively control the opening and closing of the lumen 13, thereby selectively regulating the flow of the insufflation gases therethrough. The valve 120 defines an opening therein that allows fluid or gas communication therethrough. The opening inside the valve 120 is dynamically adjustable, and its size can be selectively rendered to regulate the flow rate of the insufflation gases therethrough. The valve 120 may be a globe valve. A small opening inside the valve 120 results in a low flow rate, whereas a large opening inside the valve 120 results in a high flow rate. The opening within the valve 120 can be completely open to attain a maximum flow rate therethrough, or completely closed to result in a flow rate of zero. In one instance, when the valve 120 is completely open, the valve 120 allows fluid or gas communication between the lumen 13 and the extra-corporeal environment at a maximum output flow rate, such that the insufflation gases can rapidly exit from the insufflated cavity to the extracorporeal environment through the filtering agent present in the lumen 13. When the valve 120 is completely closed, the valve 120 completely obstructs the passageway between the lumen 13 and the extra-corporeal environment, thereby preventing outlet of the insufflation gases from the insufflated cavity. Further, the size of the opening within the valve 120 can be dynamically selected anywhere between the completely open state and the completely closed state to adjust the flow rate accordingly. As illustrated in FIG. 3, the valve 120 is operated manually by a surgeon, as the surgeon decides the appropriate output rate of the insufflation gases exiting from the peritoneal cavity.

Figure 4:
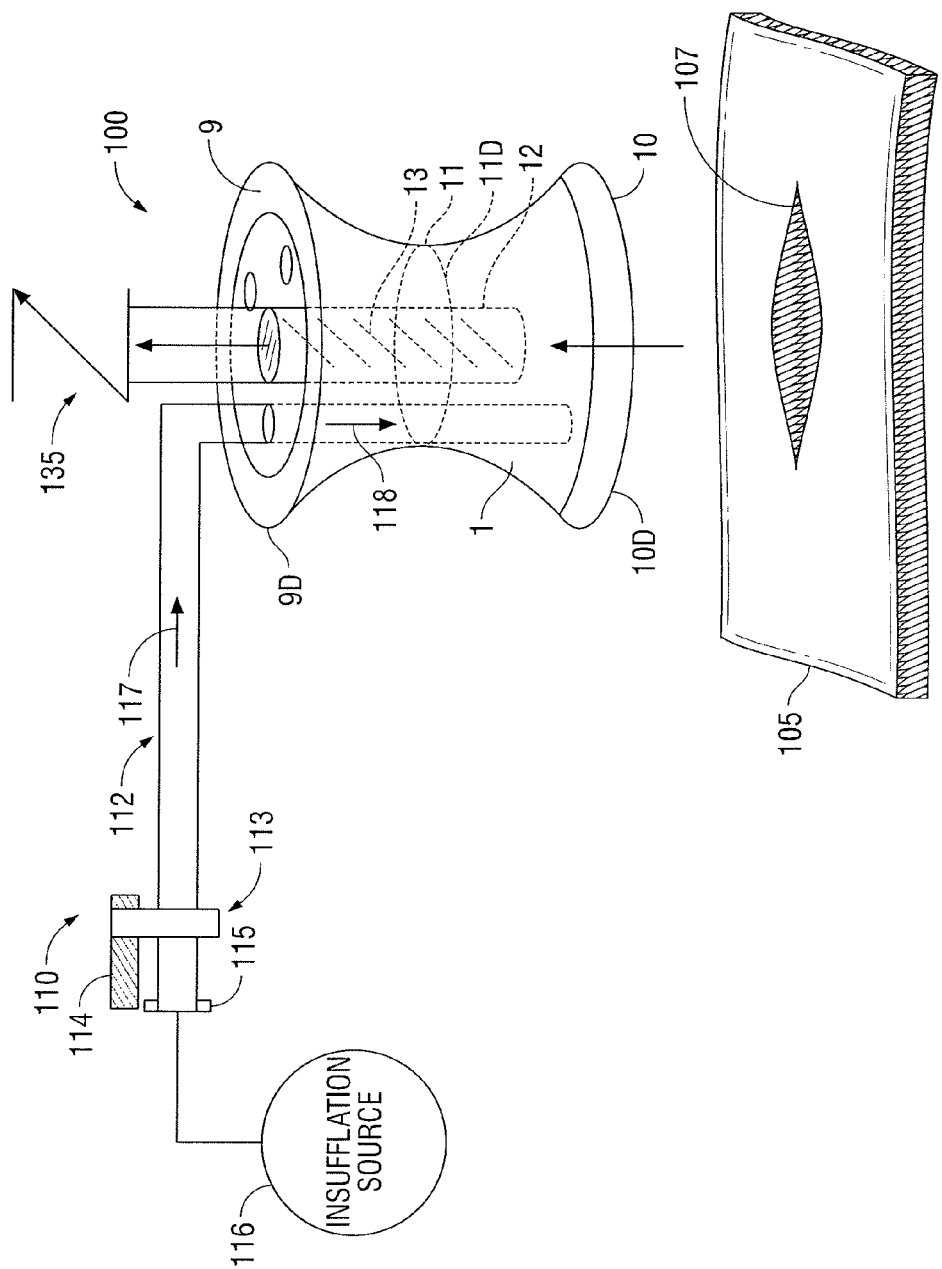
FIG. 4 shows a perspective view of the single port device of FIG. 1 in connection with a check valve.

In a certain embodiment, the valve is a self-controlled valve that automatically controls the size of the opening within the valve without intervention from a user. For instance, the valve may be a check valve 135 as illustrated in FIG. 4, or a spring check valve. The check valve 135 is associated with a cracking pressure which corresponds to a predetermined differential pressure across the valve, that is, a predetermined differential pressure between the peritoneal cavity and the ambient pressure in the operating room. The check valve 135 opens when a detected differential pressure across the valve attains or reaches beyond the predetermined cracking pressure. By contrast, the check valve 135 closes when the differential pressure is below the predetermined cracking pressure. For instance, the valve 135 opens when the patient's body cavity is sufficiently insufflated attaining a desired insufflation pressure therein, which is higher than the ambient pressure, resulting in a differential pressure greater than or equal to the cracking pressure. The valve 135 closes when the insufflation pressure significantly declines after a certain amount of the insufflation gases is released from the body cavity into the extra-corporeal environment, resulting in a differential pressure less than the cracking pressure.

Figure 5:
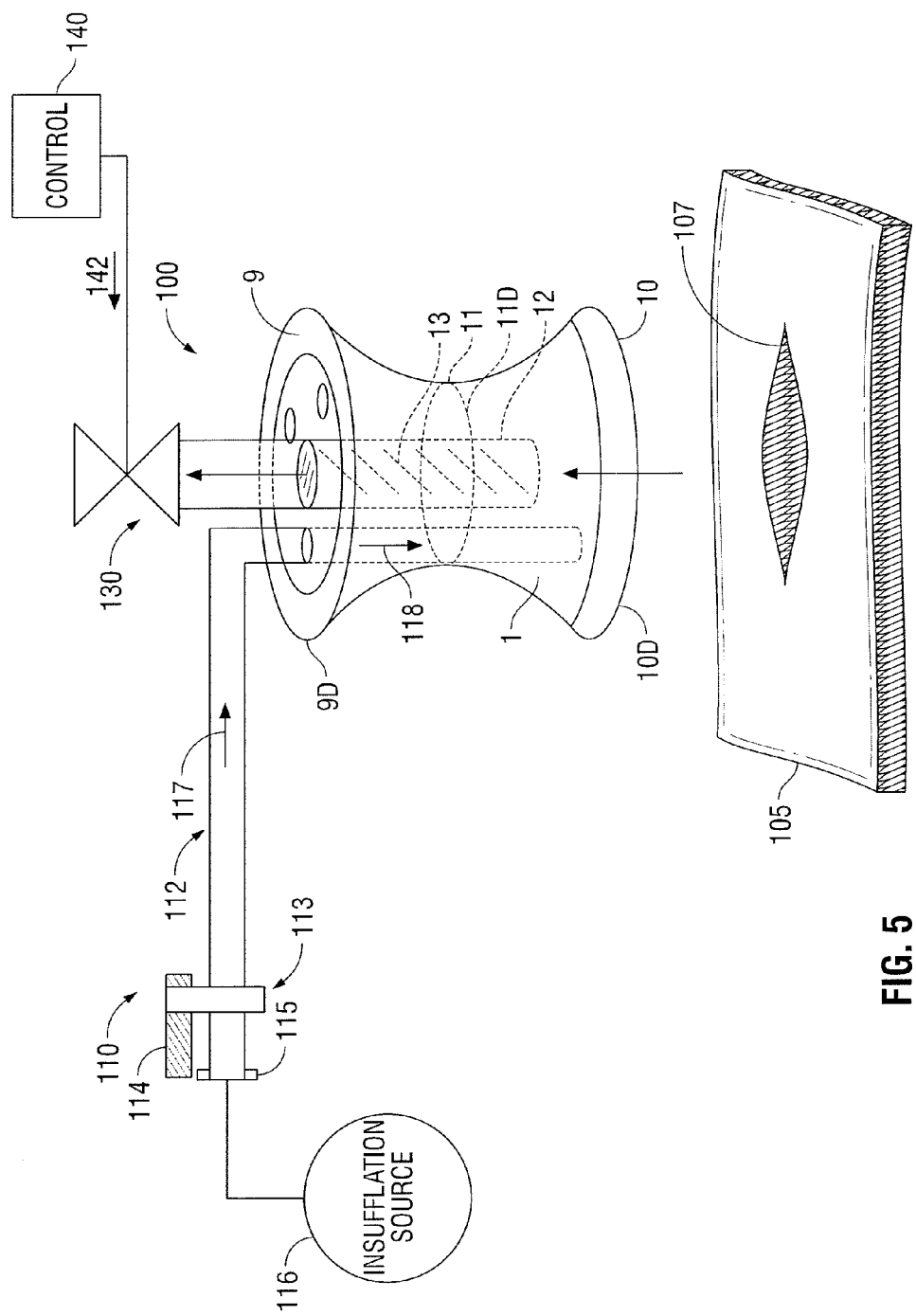
FIG. 5 shows a perspective view of the single port device of FIG. 1 in connection with an electrically operated external valve.

In another embodiment, the valve is an electrically operated valve 130, as illustrated in FIG. 5, driven by a control unit 140 through a control signal 142. The control signal 142 instructs the valve 130 to adjust the size of its opening, which, in turn, regulates the flow rate through the lumen 13. In one example, the control unit 140 may send the signal 142 at a predetermined time interval to periodically open and close the lumen 13. In another example, the control unit 140 may detect changes in insufflation pressure or temperature, then send the signal 142 to the valve 130 to adjust the size of the opening therein, thereby adjusting the flow rate accordingly.

Figure 6:
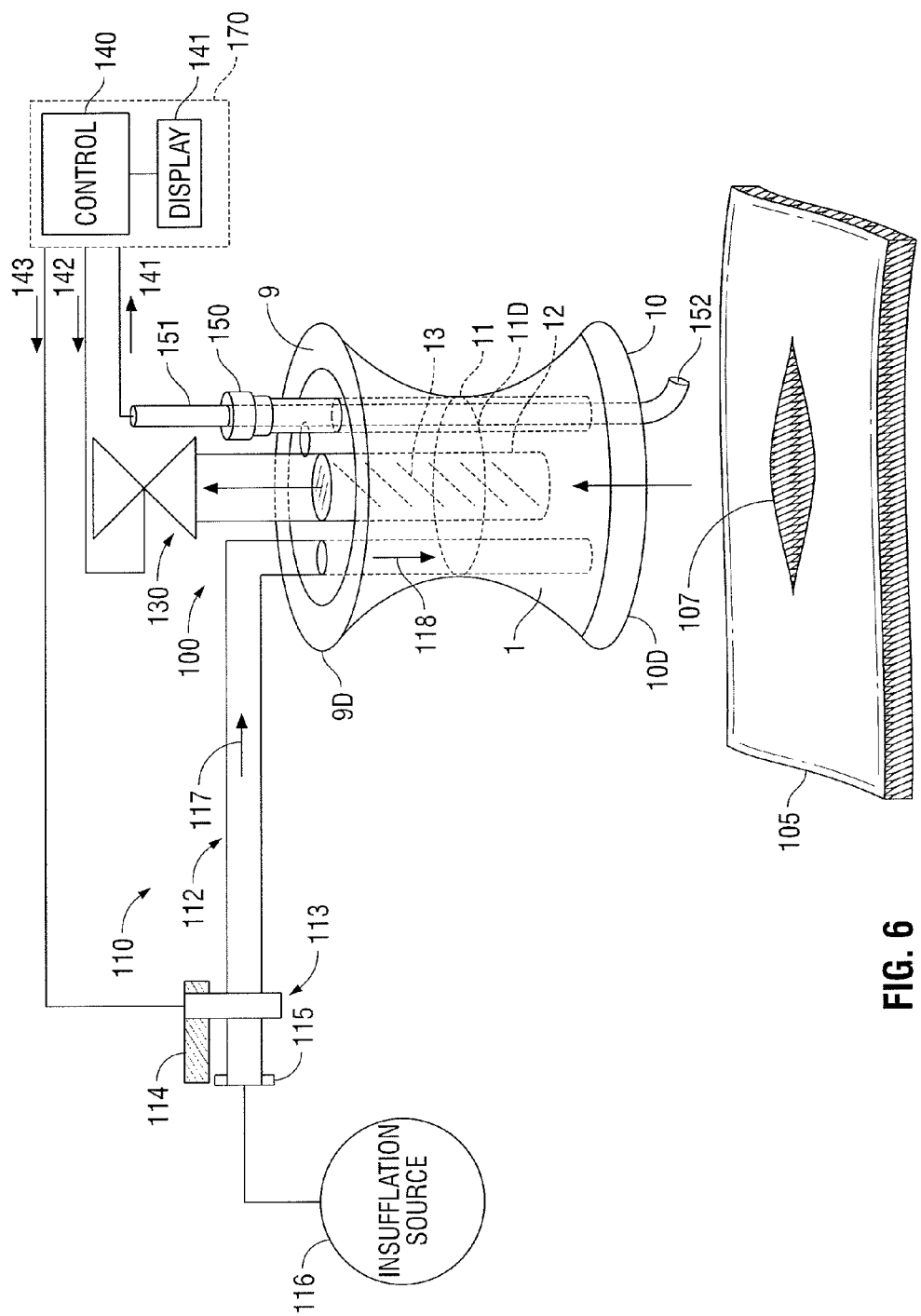
FIG. 6 shows a perspective view of the single port device of FIG. 5 in connection with a work station.

With reference to FIG. 6, the control unit 140 may be part of a work station 170 which comprises the control unit 140 as well as a display unit 141. The control unit 140 is operatively connected with the valve 130, the insufflation instrument 110 as well as an endoscope 151 disposed within the seal anchor member. The control unit 140 regulates the valve 130 through signals 142 as discussed above. The control unit 140 is also configured to transmit signals 143 to the insufflation instrument 110 to specifically control the stopcock 114, which, in turn, regulates the flow of insufflation gases therethrough. The endoscope 151 is disposed within a cannula 150 mounted on the seal anchor member. The endoscope 151 is configured to transmit images of the peritoneal cavity captured by its camera 152 located at its distal end to the control unit 140 through communication signals 141. The control unit 140 may then display the transmitted images on a display unit 141, e.g., a LCD monitor, for users to view. The control unit 140 is also configured to analyze the transmitted images to determine if there is a need to adjust the input and output rate of insufflation gases. Based on the analysis, the control unit 140 instructs the valve 130 and the insufflation instrument 110 accordingly. In one example, the control unit 140 analyzes the transmitted images by first assigning digital data values to each pixel of the image based on its color, then compares the data values to a predetermined data range that corresponds to an obscured view of a peritoneal environment contaminated by smoke or particles. On the one hand, if the assigned data values fall within the predetermined range, the control unit 140 then concludes that there is a need to remove the contaminants from the peritoneal cavity. Accordingly, the control unit 140 instructs the valve 130 to adapt to its maximum open position, thereby filtering out the contaminants at the maximum output rate. Additionally, the control unit 140 may conclude that there is a need to introduce more insufflation gases from the insufflation instrument 110 to the peritoneal cavity to compensate for the escape of the contaminated insufflation gases. Based on this conclusion, the control unit 140 opens the stopcock 114 if it was closed to permit insufflation gases to pass therethrough or opens to stopcock 114 to a wider degree if it was already open to increase the input rate of the insufflation gases. On the other hand, if the assigned data values are outside of the predetermined range, the control unit 140 then concludes that the peritoneal cavity is clean thus no need to filter out the insufflation gases from the peritoneal cavity. Accordingly, the control unit 140 sets the valve 130 to its closed position impeding release of the insufflation gases from the peritoneal cavity. The control unit 140 may also turn off the stopcock 114 if a desired insufflation pressure within the peritoneal cavity is reached.

Figure 7:
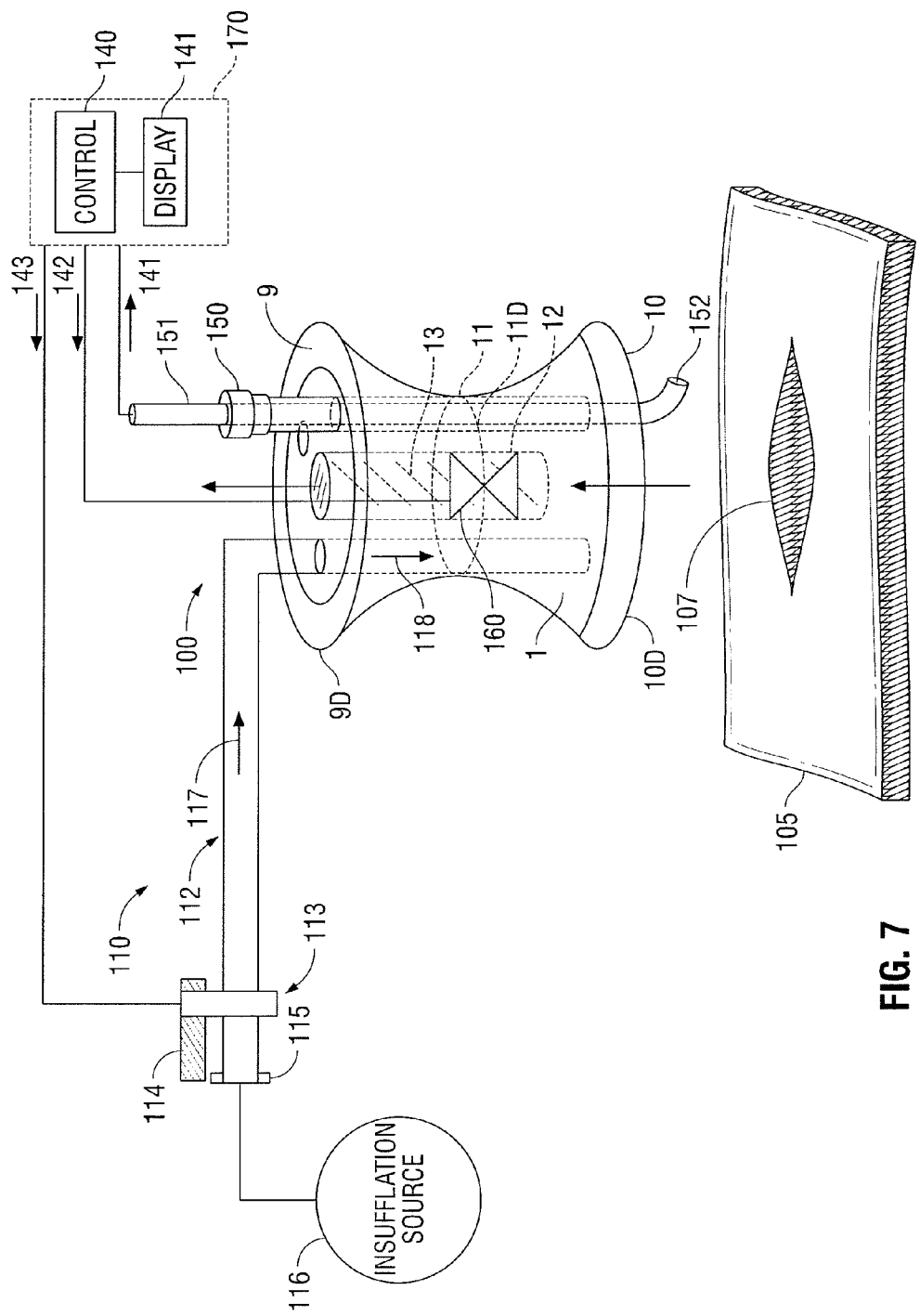
FIG. 7 shows a perspective view of the single port device of FIG. 1 in connection with an electrically operated internal valve and further in connection with a work station.

In another embodiment, the valve can be an integrated valve 160 located within the vent 12, as illustrated in FIG. 7. Similar to the external valve 130 illustrated in FIG. 6, the integrated valve 160 in FIG. 7 is operatively connected with a work station 170 that controls the insufflation instrument 110 and the valve 160 based on the analysis of images captured by the endoscope 151.

In a certain embodiment, the lumen 13 of the integral vent 12 is rendered to have a relatively small diametric dimension. The lumen 13 of a small diametric dimension permits continuous release of the insufflation gases at a controlled minimal speed. The insufflation gases may be continuously introduced into the body cavity. The insufflation gases are first introduced at an input rate relatively higher than the normal input rate used in other typical minimally invasive procedures. As a result, due to the small dimension of the lumen 13 as well as the higher than normal input rate, the insufflation gases are released at an output rate considerably lower than its input rate. Based on this configuration, because the input rate is greater than the output rate, the pressure within the patient's cavity will gradually increase to reach a desired insufflation volume and a desired insufflation pressure. Once the desired insufflation volume and the desired insufflation pressure are reached, the input rate of the insufflation gases is reduced to be the same as the output rate for purposes of maintaining the desired insufflation pressure. Because of the continuous inflow of the clean insufflation gases and the continuous outflow of the contaminated insufflation gases, impurities such as smoke or other incidental byproducts due to operation are automatically and continuously removed from the patient's cavity, resulting in a clean interior environment within the patient's cavity at all times.

Those skilled in the art, having the benefit of the teachings of the present invention as herein and above set forth, may effect modifications thereto. Such modifications are to be construed as lying within the scope of the present invention, as defined by the appended claims.

Although specific features of the single port device are shown in some of the drawings and not in others, this is for convenience only as each feature may be combined with any or all of the other features in accordance with the aspects of the present disclosure. Other embodiments will occur to those skilled in the art and are within the following claims.

What is claimed is:

1. A laparoscopic port device comprising:
    a body having a proximal end and a distal end, the body substantially composed of a filtering agent, the filtering agent configured to retain particulate contaminates present in insufflation gases passing through the body, wherein at least a portion of the filtering agent includes a compound that treats or reacts with particulate contaminants present in the insufflation gases.

2. The laparoscopic port device of claim 1, further comprising a lumen extending through the body, the lumen configured to receive a surgical instrument therethrough.

3. The laparoscopic port device of claim 1, wherein the body is formed from a material selected from the group consisting of a rigid material, a semi-rigid material, and a compliant material.

4. The laparoscopic port device of claim 1, wherein the body further defines a plurality of lumens extending through the body to enable a plurality of surgical instruments to simultaneously traverse the body.

5. A laparoscopic port device comprising:
    a body having a distal end and a proximal end; and
    a filtering agent integrally formed in the body and establishing fluid communication between the distal and proximal ends of the body and allowing direct flow of insufflation gases between the distal end and the proximal end of the body, the filtering agent configured to retain particulate contaminates present in insufflation gases, wherein at least a portion of the filtering agent includes a compound that treats or reacts with particulate contaminants present in the insufflation gases.

6. The laparoscopic port device of claim 5, wherein the body defines a lumen extending through the body, the lumen configured to receive a surgical instrument therethrough.

7. The laparoscopic port device of claim 5, wherein the body is formed from a material selected from the group consisting of a rigid material, a semi-rigid material, and a compliant material.

8. The laparoscopic port device of claim 5, wherein the body further defines a plurality of lumens extending through the body to enable a plurality of surgical instruments to simultaneously traverse the body.

* * * * *